United States Patent [19]

Davidson et al.

[11] Patent Number: 5,426,309

[45] Date of Patent: Jun. 20, 1995

[54] METHOD AND APPARATUS FOR INSPECTING THE DEPTH OF THE SURFACE OF CYLINDRICAL OBJECTS

[75] Inventors: Iain S. Davidson, Preston; Alan Higson, Lancashire; Thomas G. Rice; Graeme M. Wigg, both of Preston, all of United Kingdom

[73] Assignee: British Nuclear Fuels plc, Cheshire, United Kingdom

[21] Appl. No.: 95,860

[22] Filed: Jul. 23, 1993

[30] Foreign Application Priority Data

Jul. 24, 1992 [GB] United Kingdom ................ 9215832

[51] Int. Cl.6 .............................................. G01N 21/88
[52] U.S. Cl. ...................................... 250/562; 356/237
[58] Field of Search ....................... 250/562, 563, 561; 356/73, 376, 445, 237, 384, 385; 209/579, 586, 587

[56] References Cited

U.S. PATENT DOCUMENTS

| | | |
|---|---|---|
| 4,162,126 | 7/1979 | Nakagawa et al. |
| 4,226,539 | 10/1980 | Nakagawa et al. ................ 356/445 |
| 4,532,723 | 8/1985 | Kellie et al. ............................ 356/73 |
| 4,660,970 | 4/1987 | Ferrano . |
| 4,982,103 | 1/1991 | Meiffren et al. . |
| 5,229,619 | 7/1993 | Van Amstel ....................... 356/376 |

FOREIGN PATENT DOCUMENTS 2080943 2/1982 United Kingdom .
2181835 4/1987 United Kingdom .

OTHER PUBLICATIONS

Bottlinger et al.; "Signale Richtig Interpretieren"; Laser Praxis, No. 1, 1 Jun. 1990, pp. LS54–LS55.
Goodman; "Scanning Laser Illumination System"; IBM Technical Disclosure Bulletin; vol. 27, No. 4B, 1 Sep. 1984; pp. 2643–2644.

Primary Examiner—David C. Nelms
Assistant Examiner—Que T. Le
Attorney, Agent, or Firm—Nixon & Vanderhye

[57] ABSTRACT

Apparatus for the inspection of the surface of a cylindrical object which comprises a rotator for rotating the object to be inspected about its axis, a projector for projecting an incident beam of radiation to form a spot on the surface of the object whilst the object is rotating, a device for providing, relative to the object when being rotated, translation of the spot formed by the projection means, a detector for detecting a scattered beam of radiation which comprises radiation of the incident beam after scattering by the surface of the object and a processor for deriving from the detection by the detector of the scattered beam information about the depth of the surface of the inspected object in the region where the incident beam spot is applied.

25 Claims, 5 Drawing Sheets

METHOD AND APPARATUS FOR INSPECTING THE DEPTH OF THE SURFACE OF CYLINDRICAL OBJECTS

BACKGROUND OF THE INVENTION

1. Field of the Invention

The present invention relates to the inspection of cylindrical objects and is concerned with apparatus and a method for inspecting the surface of cylindrical objects.

2. Discussion of Prior Art

In the production of certain cylindrical objects it is necessary to keep surface defects to a minimum. For example, in the production of nuclear fuel pallets surface cracks or chips are undesirable. Rows of such pellets are loaded into tubes usually made of stainless steel or zirconium alloy to form fuel pins and it is essential that the pellets do not disintegrate during mechanical handling, loading or sealing of the tubes, whereby damage to the tubes during further processing of the fuel pins is prevented.

SUMMARY OF THE INVENTION

The purpose of the invention is to provide a technique for the detection of defects on the surface of cylindrical objects especially objects manufactured in large quantities such as nuclear fuel pellets.

According to the present invention there is provided apparatus for the inspection of the surface of a cylindrical object which comprises means for rotating the object to be inspected about its axis, projection means for projecting an incident beam of radiation to form a spot on the surface of the object whilst the object is rotating, means for providing relative to the object when being rotated translation of the spot formed by the projection means, and detector means for detecting a scattered beam of radiation which comprises radiation of the incident beam after scattering by the surface of the object and means for deriving from the detection by the detection means of the scattered beam information about the depth of the surface of the inspected object in the region where the incident beam spot is applied.

Desirably, the incident beam provided by the projection means and the scattered beam detected by the detector means are at an angle to one another, whereby the position of incidence of the scattered beam on the detector means provides a measure of the depth of the surface of the object from which the incident beam spot is scattered. The detector means in this case is desirably a position sensitive detector which produces an output which represents the lateral position of the detected spot formed by the scattered beam which itself is a measure of the depth of the object reflecting surface (relative to a datum value).

The projection means may comprise a source of collimated visible light which may conveniently be a laser light source, eg a semiconductor laser. The output beam of the laser light source may be focused by a lens onto the surface of the object to be inspected.

Alternatively the projection means may comprise a source of invisible radiation, eg infra-red radiation.

The scattered beam may be focused by a lens onto the detector means.

The beam provided by the projection means may be provided as a c.w. (continuous) output. The scattered beam may be sampled at discrete time intervals, eg at a frequency of between 10 and 100 samples per second, the samples thereby representating measurements at discrete positions on the surface of the inspected object.

In this way a series of measurements or readings may be made of the depth below an arbitrary fixed datum position to the surface of the object at a series of measurement points on the surface of the object. The points are on a locus which is in the form of a helix following the outside surface of the object. The pitch of the helix may be set by adjusting the translational speed of the helix. The distance between successive measurement points on the helix may be set by adjusting the rotational speed of the object or by adjusting the frequency of sampling the scattered beam.

The present invention beneficially provides a technique for detecting defects on the surface of a cylindrical object. It may be employed to examine automatically without human handling the curved surface of a cylindrical object presented automatically to the apparatus and to determine whether or not the surface is in accordance with pre-defined criteria. For a defect-free surface on a cylinder of constant cross-sectional radius the depth readings for all points on the surface of the object will be equal. However, where surface defects such as chips or cracks exist, the depth readings for points on the surface which are located in the defect will be different from and usually greater than those for points where no defects exist. Thus, the presence of defects on the surface of the object may be detected by taking a series of surface depth readings in the manner described.

The output sequence of values representing depth readings at a succession of points on the surface of the object may be processed to determine the presence of defects which are unacceptable. Thus, it may be determined from the said sequence how many consecutive depth readings in a circumferential sense and/or in an axial sense differ from the expected mean depth reading and the dimensions of the defect in terms of circumferential, axial length and the surface area may be calculated. Where one of the dimensions and/or the area is greater than a pre-set acceptable limit the object may be rejected. The comparison of the output values representing a sequence of surface depth readings with an expected mean sequence of values for a defect-free surface, and the determination of the dimensions and area of any defect and the comparison of the dimensions with pre-set acceptable limits may be carried out by signal processing logic comprising of incorporated within the said means for deriving information.

The present invention is particularly suited for the automatic inspection of nuclear fuel pellets, especially pellets for use in reactors of the so-called PWR type. For example, such pellets typically have a length of about 13.5 mm and a diameter of about 8 mm. A series of surface depth measurements may be taken at some 4,000 points over the curved surface of the pellet. According to pre-set acceptance criteria such a pellet is to be rejected if the overall lost circumferential area, due to a single or multiple defect, exceeds 10.0 square millimeters. Defects with a maximum dimension in any direction of 0.5 mm or less may be excluded from the lost area summation in this calculation.

Nuclear fuel pellets inspected by the technique of the present invention may include mixed oxide or so-called "MOX" fuel pellets (which include mixtures of uranium and plutonium oxide), and may also include fuel pellets for use in Advanced Gas Cooled Reactors (AGR), BWR and other water-cooled reactors.

The cylindrical objects inspected by the technique of the present invention may have deliberate features, eg end chamfers or grooves applied to their outside surface. For example, in a supply of AGR nuclear fuel pellets certain selected pellets have a circumferential surface groove of V-shaped cross-section. Besides searching for defects, the present invention allows the dimensions of such features to be checked and compared automatically with the dimensions set in the product specification. If it is detected that the detected dimensions are wrong, eg because too much or too little material has been machined from the object during its previous manufacture, the deviation from the desired dimension(s) may be calculated and the error used to adjust the machine, eg grinder, employed in manufacture to apply the feature on the surface of the objects.

The means for providing translation of the spot of the beam of radiation formed by the projection means may comprise means for moving the object, when in a position to be inspected by the spot, along an axis substantially parallel to the axis of the object whereby the object moves past the spot. Alternatively, or in addition, the means for providing translation of the spot may comprise means for moving the projection means along an axis substantially parallel to the axis of the object when in a position to be inspected by the spot whereby the spot moves along the object. The said position may be considered as an inspection station or location. In each case the spot traces a helix around the rotating object.

The means for rotating the objects may in one form of the present invention comprise adjacent rollers and means for rotating the rollers in the same sense whereby objects placed on the rollers rotate on their axes with the rollers. The rollers may be mounted on a base which may be moved at constant speed by a suitable linear actuator in a known way along an axis, eg by a leadscrew providing movement along an axis parallel to the axes of the rollers and the object thereon. At the end of transverse provided by the actuator the linear movement may be reversed whereby the base is returned to a re-start position.

A plurality of objects, eg two to five objects, may be placed on the same rollers for inspection by the apparatus according to the present invention in the form including rollers. Such objects may each have its own dedicated inspection station and inspection arrangement comprising projection means and detection means. The objects may be placed together on the rollers. Alternatively, one inspection arrangement may be shared between two or more objects. For example, each object in the plurality may be inspected in turn on the rollers by the same spot whilst another is being removed and replaced and so on.

In the form of the invention including rollers the objects may be placed on and removed from the rollers by a pick and place machine. The objects may be obtained from a pick up position and moved in a lateral direction substantially perpendicular to the axes of the rollers when they are placed on and subsequently removed from the rollers. The objects may be inspected and the results of the inspection may be obtained prior to removal from the rollers. If the result of the inspection is that the object is acceptable it may be removed by the pick and place machine to an acceptance location. If the result is that the object is unacceptable it may be removed by the pick and place machine to a reject location. Suitable signals from the inspection apparatus may be applied to operate the pick and place machine through a suitable known controller, eg a programmable logic controller (plc), to control where the objects are deposited. A plurality of objects may be deposited together at the acceptance location and/or at the reject location as appropriate.

In the form of the invention including rollers a containment may be provided around the rollers and the objects, where nuclear fuel pellets, deposited on and removed thereform. Such a containment protects the outside environment from radioactivity hazards presented by the pellets. In this form the ends of the rollers may conveniently extend to project outside the containment whereby the machinery provided to rotate and translate the rollers may be manually inspected and maintained outside the containment.

Where a plurality of objects are placed together on rollers there may be end stops provided adjacent to the rollers to define the extremities of the inspection station whereby the ends of the objects when in position on the rollers at the inspection stations may be confined to remain between the extremities of the station.

In an alternative form of the apparatus according to the present invention simultaneous rotation and translation of the objects to be inspected may be carried out in a known way by using apparatus comprising a continuous belt which may be moved along a track which is inclined relative to the horizontal plane, and a plate extending across the surface of the belt. Desirably, the angle of the plate relative to the side edges of the belt is adjustable. Objects are fed onto the belt above the plate and become supported on the belt by the plate. Movement of the belt provides rotation of the object about its axis and deviation from the horizontal plane of the line representing the projection of the edge of the plate across the belt allows lateral translational movement of the objects by sideways slippage. The direction of the translation may be in a positive or negative sense depending on whether the plate is tilted downward to the left or to the right. The speed of rotation of the objects may be adjusted by adjusting the speed of the belt and the translational movement may be adjusted by adjusting the angle of the plate relative to the edges of the belt.

Alternatively, the translational movement may be produced by varying the angle of the line of belt movement, relative to a fixed position of the plate. In both alternatives it is the angle between the belt and the plate which provides the degree of translation.

In the automatic handling of nuclear fuel pellets, the pellets may be conveyed to a pellet inspection apparatus for inspection in accordance with the present invention by the Applicants' so-called "Cushion Transfer" TM technique which is described in UK Patent Specification No. 2223998A.

In the form of the invention comprising rollers the nuclear fuel pellets may be conveyed to a pick up location and may be transported away from an acceptance location by Cushion Transfer conveyers.

In the form of the invention wherein pellets are rotated and translated by a belt and plate, a single Cushion Transfer conveying track may be divided into a plurality of tracks, eg five tracks, each track feeding pellets to its own inspection station. Each station may include its own means for rotating and translating the pellets and its own projection and detection means. The pellets moving along the different tracks may be recombined onto one track after inspection, although pellets bearing a detected defect may be automatically removed from their track, eg by operating a chute, after passing through the inspection apparatus. This operation may be carried out by counting the number of pellets introduced into the inspection apparatus, recording the count number of defective pellets and counting the number of pellets leaving the apparatus until the defective pellet is reached. These operations may be carried out automatically by use of counters and a count recorder. Such a system is known as "first in first out" ("fifo").

Desirably, each inspection apparatus including projection and detector means is calibrated in use from time-to-time using calibration pellets of known dimensions having a defect-free surface and also defects of known dimensions.

BRIEF DESCRIPTION OF THE DRAWINGS

Embodiments of the present invention will now be described by way of example with reference to the accompanying drawings, in which.

DETAILED DISCUSSION OF PREFERRED EMBODIMENTS

Figure 1:
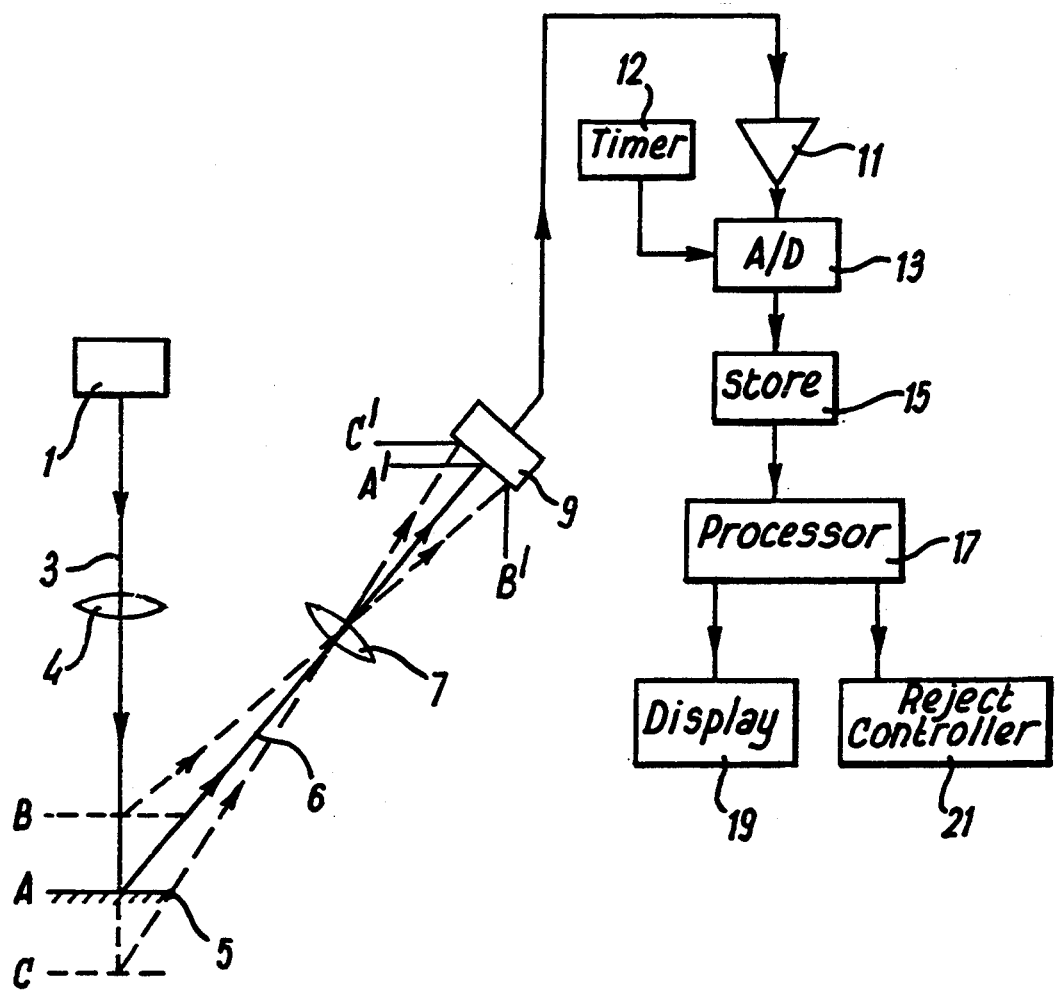
FIG. 1 is a schematic front view of a nuclear fuel pellet inspection apparatus.

As shown in FIG. 1 a semiconductor laser 1 produces an output beam 3 having a wavelength of typically 670 mm. The beam 3 is focused by a lens 4 as a spot onto the curved surface of the pellet to be measured. The surface of the pellet is represented by numeral 5. The beam 3 is scattered by the pellet surface 5 as scattered light 6 toward a lens 7 where it is focused to a point or spot onto a position sensitive detector 9.

When the scattering pellet surface 5 is at the expected mean position as represented by symbol A in FIG. 1 the scattered light 6 falls on the detector 9 at a position A'. However when the scattering pellet surface 5 rises to a position B or falls to a position C (both shown dashed in FIG. 1) the scattered light 6 is incident on the detector 9 at positions B' and C' respectively. The distances between the positions A' and C' and A' and B' on the detector 9 are respectively measures of the depth of the pellet surface 5 at positions B and C relative to that at position A. Thus, the signal which is the output of the position sensitive detector 9 for each measurement point on the surface of the pellet 5 represents the relative depth of the surface at that position.

The output of the detector 9 is amplified by an amplifier 11 and an analogue signal, proportional to the distance of the surface 5 from the detector 9 is fed to a microprocessor based signal processor 17. Frequent samples of the signal are taken by the signal processor 17, through an analogue to digital convertor 13, typically acquiring around 4000 samples per pellet such that the pellet surface is inspected in 400 micron steps. A series of algorithms are used in the signal processor 17 to compare the samples with the expected mathematical model from a defect-free surface and the result of this comparison is shown on a display 19. The expected mathematical model is periodically tested by using calibration standards which relate to known perfect pellets. The mechanical settings of the system, such as belt speed and angle of the belt are also periodically tested. The result, where this shows that a detected defect is unacceptable, may also be employed to provide an output signal which triggers a reject controller 21 to provide rejection of the measured pellet 5 by using a counting procedure in the manner described above.

The result may also be used to eliminate unacceptable pellet variations, for example in pellet diameter or pellet taper, and unacceptable feature variations such as groove depth relative to the pellet surface. Pellets having such unacceptable variations may be rejected.

The beam 3 falls continuously as a spot on the surface 5 of the pellet. Because the pellet is rotating and translating the spot traces out a helix. Discrete points along the helix are sampled by sampling the output of the detector 9 at suitable intervals, eg 40 times per second by the timer 12. This sampling procedure is illustrated in FIG. 2.

Figure 2:
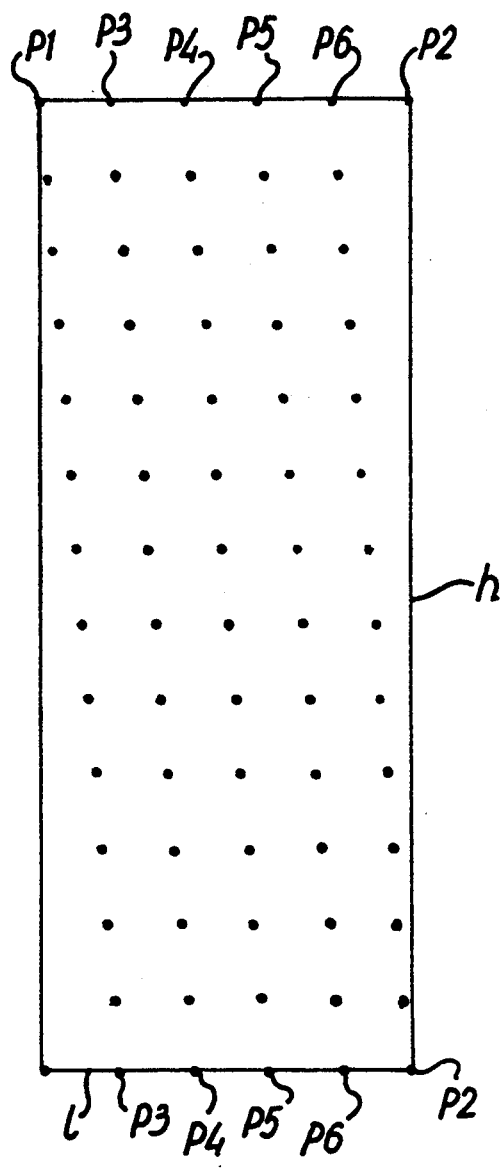
FIG. 2 is a diagram representing in two dimensions the curved surface area of the nuclear fuel pellet and the points of inspection on the pellet.

The rectangle having the opposite pairs of sides l and h in FIG. 2 represents in two dimensions the overall curved surface area of the inspected pellet. The dimension l represents the length of the pellet and the dimension h represents the circumferential distance around the surface of the pellet. A sequence of relative depth measurement of the surface of the pellet is made at points P throughout the surface area. The sequence begins at the left hand end of the pellet (as represented in FIG. 2) at a point P1 and then proceeds in a series of discrete steps following a helix until the right hand end of the pellet is reached at a point P2.

Intermediate points, P3, P4, P5 and P6 are each at the end of various turns of the helix and therefore appear at both the top and the bottom of edges of the diagram. Thus, the locus tracing the line of the points from P1 to P3 at the bottom edge continues from P3 at the top edge to P4, and so on.

In practice, the plot on the surface of the pellet may contain a larger number of points P of measurement than as shown in FIG. 2.

Figure 3:
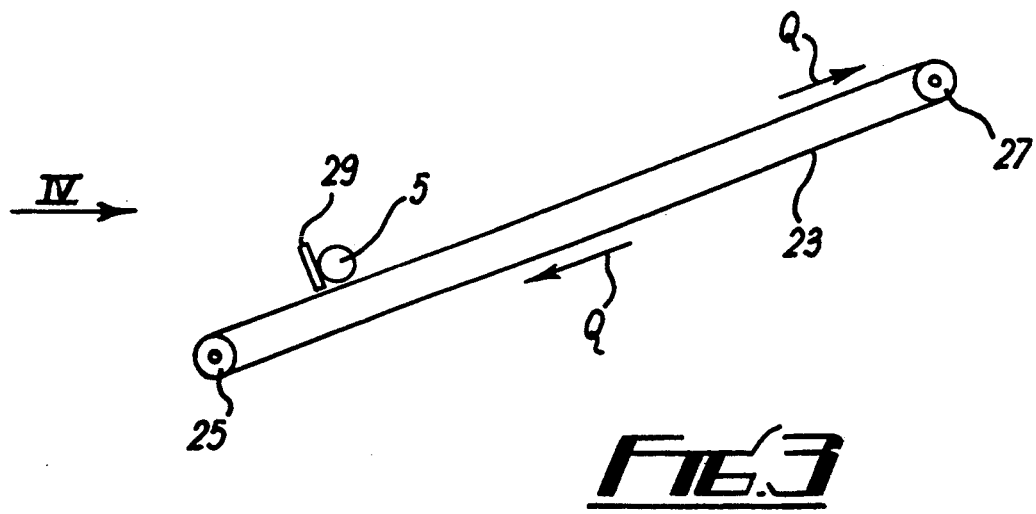
FIG. 3 is a side view and FIG. 4 is a front view (in the direction IV shown in FIG. 3) of an arrangement for rotating and translating the pellets in the apparatus of FIG. 1.
Figure 4:
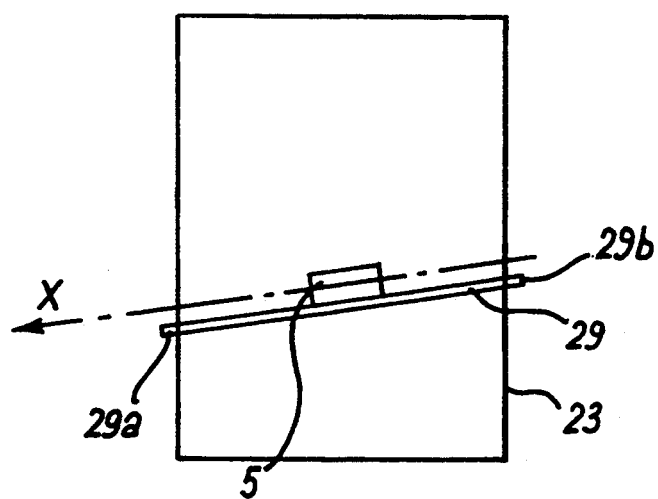

FIGS. 3 and 4 show one form of device for rotating and translating the pellets 5 for use with the apparatus shown in FIG. 1.

A continuous rubber belt 23, driven at a constant velocity by a servo motor (not shown) moves in the direction of the arrows Q around rollers 25, 27.

The belt 23 is inclined by virtue of the roller 27 being at a height above the roller 25. A pellet 5 to be inspected is supported on the belt 23 by a plate 29. The angle of the plate 29 relative to the side edges of the belt 23 is adjustable but in FIG. 4 the angle is adjusted so that one end 29a is lower than the other end 29b. The pellet 5 is caused to rotate by the movement of the belt 23 and to be moved laterally or translated in a direction X parallel to its axis by lateral slippage down the plate 29. If the angle of the plate 29 is changed so that the end 29a is above the end 29b then the lateral movement of the pellet 5 is in the opposite direction.

In the apparatus described with reference to FIG. 1 the components comprising the laser 1, lens 4, lens 7, detector 9 and amplifier 11 may be provided as a commercially available height measuring system such as a Keyence LC 2000 laser displacement sensor. A resolution of $8 \times 10^{-4}$ mm may be satisfactorily achieved with such a system.

In operation of the apparatus, in order to ensure that mechanical vibration or electrical noise will not be registered as a defect, at least two unacceptable samples, on consecutive turns of the pellet, must be detected before action is taken to reject the pellet. Since the surface speed of the belt remain constant and the diameter of the pellet is known, the number of samples per revolution of the pellet is known and may be used to ensure that two signals correlate for one defect. In order that this may be effected, the helix spacing and the intersample period must be short enough to ensure the required minimum size of defect is detected.

The signal processing unit may comprise a Motorola 68000 processor running at 10 MHz. In operation the signal processor handles the sample processing in real time and then compares the results obtained in a decision tree, immediately after the pellet has been inspected, in order to indicate the nature of the fault observed. The pellet is rejected, if necessary, by operating a reject mechanism, and cumulative records are kept of the different types of defect detected, as well as the location in which the defect was found on the pellet eg edge, body, groove.

In practice an inspection time of 5 seconds per pellet has been achieved using the aforementioned signal processor. A faster processor or the use of parallel processing (transputers) would enable a higher throughput of pellets or finer defect resolution.

Figure 5:
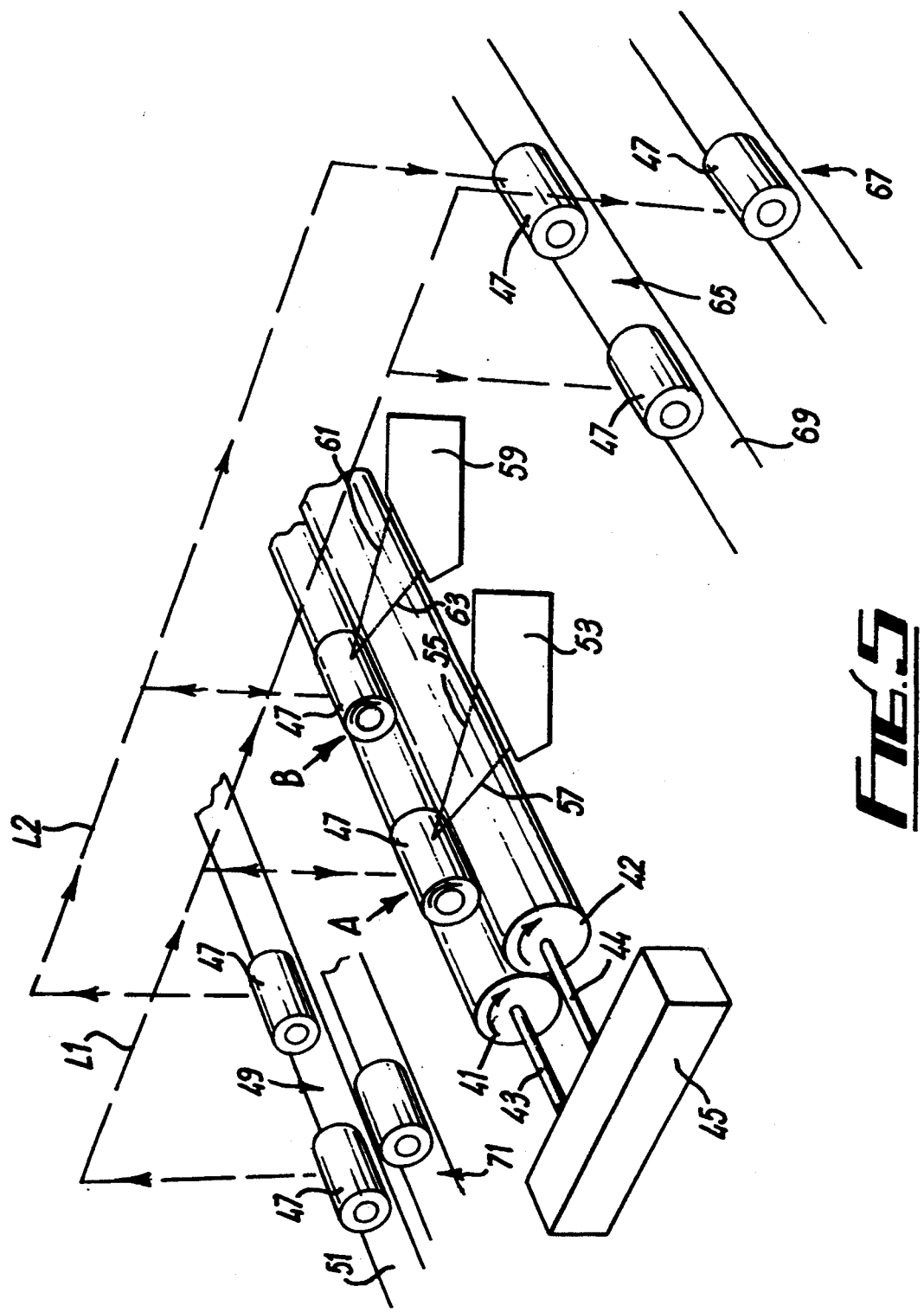
FIG. 5 is a perspective view of an alternative inspection apparatus embodying the present invention.

As shown in FIG. 5 an alternative form of the apparatus embodying the invention comprises rollers 41, 42 rotated by shafts 43, 44 driven by a drive unit 45 and moved linearly parallel to their own axes (as described with reference to FIG. 6 below). Nuclear fuel pellets 47 are placed on the rollers 41, 42 the positions A, B etc defining inspection stations on the rollers 41, 42. The pellets 47 are obtained from a pick-up station 49 to which they are conveyed by a Cushion Transfer conveyer 51. The pellets 47 are picked up from the station 49 by a pick and place machine (not shown) which carries the pellets 47 along the directions indicated by dashed lines L1 and L2 etc (two only shown). Each pellet 47 placed at the inspection station A is inspected in the same manner as described above with reference to FIGS. 1 and 2 using an inspection device 53 incorporating components similar to the laser 1, lens 4, lengs 7 and detector 9. Lines 55, 57 indicate respectively the output and scattered laser beams in the inspection procedure at Station A. Similarly, each pellet 47 placed at the inspection station defined by position B is inspected using an identical inspection device 59 and lines 61, 63 indicate respectively the output and scattered laser beams in the inspection procedure at Station B.

After inspection at the Stations A, B etc the pellets are transferred by the pick and place machine either to an acceptance station 65 or to a reject station 67 as appropriate. Accepted pellets 47 at the acceptance station 67 are subsequently conveyed away by a Cushion Transfer conveyer 69.

At suitable time intervals calibration pellets (ie defect free 'model' pellets of known dimensions and also pellets having given defects of known dimenions) are picked up by the pick and place machine from a station 71 and inspected at the stations A, B etc. so that the calibration of the inspection devices 53, 59 is accurately maintained during operation of those devices.

Figure 6:
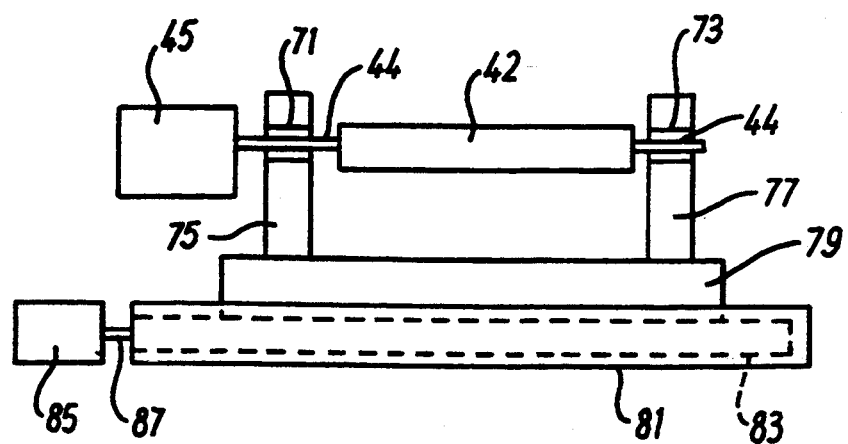
FIG. 6 is a side view of the part of the apparatus shown in FIG. 5.

FIG. 6 shows how linear as well as rotary motion is applied to the rollers 41, 42 and therefore to the pellets 47 placed thereon. As described above, the drive unit 45 drives the rollers 41, 42 by the drive shafts 43, 44 (roller 42 and shaft 44 only shown being in FIG. 6). The drive shaft 44 is supported through bearings 71, 73 by pillars 75, 77 respectively. The pillars 75, 77 are fixedly mounted on a base plate 79 which may be driven to move horizontally relative to a fixed base 81 by a leadscrew 83 incorporated within the base 81. The leadscrew 83 is driven by the rotary motion provided by a drive unit 85 acting through a drive shaft 87.

Thus, the spot of the beam 61 traces a helical path across each inspected pellet 47. When the spot has reached and passed the end of the pellet 47 it is inspecting the horizontal drive provided by the arrangement shown in FIG. 6 is reversed to return the rollers 41, 42 to a start position.

We claim:

1. Apparatus for the inspection of the surface of a cylindrical object which comprises:

means for rotating the object to be inspected about its axis, projection means for projecting an incident beam of radiation to form a spot on the surface of the object whilst the object is rotating, means for providing during rotation translation parallel to the axis of rotation of the spot formed by the projection means, detector means for detecting a scattered beam of radiation which comprises radiation of the incident beam after scattering by the surface of the object and means for deriving from the detection by the detection means of the scattered beam information about the depth of the surface of the inspected object in the region where the incident beam spot is applied.

2. Apparatus as claimed in claim 1 wherein the incident beam provided by the projection means and the scattered beam detected by the detector means are at an angle to one another, whereby the position of incidence of the scattered beam on the detector means provides a measure of the depth of the surface of the object from which the incident beam spot is scattered, the detector means comprising a position sensitive detector which produces an output which represents the lateral position of the detected spot formed by the scattered beam which itself is a measure of the depth of the object reflecting surface relative to a datum value.

3. Apparatus as claimed in claim 1 wherein the beam provided by the projection means in use is provided as a continuous output and the means for deriving includes means for sampling the output of the detector means at discrete time intervals the samples thereby representing surface depth measurements at discrete positions on the surface of the inspected object.

4. Apparatus as claimed in claim wherein said means for deriving includes means for processing an output sequence of values representing surface depth measurements to determine the presence of defects which are unacceptable.

5. Apparatus as claimed in claim 4 wherein the means for deriving including a means for determining from said sequence how many consecutive depth readings in a circumferential sense and/or in an axial sense differ from an expected mean depth reading, for calculating the dimensions of the defect and where one of the dimensions and/or the area of a defect is greater than a pre-set acceptable limit for generating a signal indicating that the object should be rejected.

6. Apparatus as claimed in claim 1 wherein said cylindrical object is a nuclear fuel pellet.

7. Apparatus as claimed in claim 1 wherein the means for providing translation of the spot of the beam of radiation formed by the projection means comprises means for moving the object, when in a position to be inspected by the spot, along an axis substantially parallel to the axis of the object whereby the object moves past the spot.

8. Apparatus as claimed in claim 1 wherein the means for providing translation of the spot comprises means for moving the projection means along an axis substantially parallel to the axis of the object when in a position to be inspected by the spot whereby the spot moves along the object.

9. Apparatus as claimed in claim 7 wherein the means for rotating the object comprises adjacent rollers and means for rotating the rollers in the same sense whereby objects placed on the rollers rotate on their axes with the rollers.

10. Apparatus as claimed in claim 1 wherein simultaneous rotation and translation of the cylindrical object to be inspected is carried out by an arrangement comprising a continuous belt which may be moved along a track which is inclined relative to a horizontal plane, and a plate extending across a surface of the belt.

11. A method for the inspection of the surface of a cylindrical object having an axis of rotation, said method comprising the steps of:
 projecting an incident beam of radiation to form a spot on the surface of the object;
 rotating the object about the axis of rotation;
 translating said beam of radiation parallel to said axis during rotation of said object, whereby the incident beam spot traces a helix around at least a portion of the curved surface of the object;
 detecting by a detector a scattered beam of radiation which comprises radiation of the incident beam after scattering by the surface of the object; and
 processing an output of the detector to provide a series of measurements of the depth of the object over the said at least part of said surface.

12. A method as claimed in claim 11 wherein the incident beam spot traces a continuous helix.

13. A method as claimed in claim 11 wherein the output of the detector is sampled at a series of discrete intervals.

14. A method as claimed in claim 11 wherein the output of the detector is processed to provide a series of measurement of the depth of the object relative to an arbitrary datum.

15. A method as claimed in claim 11 wherein said detector output is processed to provide a sequence of values representing surface depth measurement to determine the presence of defects on the surface of the objects which are unacceptable.

16. A method as claimed in claim 15 wherein the detector output is processed to determine from said sequence of values how many consecutive depth readings, in at least one of a circumferential sense and an axial sense, differ from an expected mean depth reading and to calculate the dimensions of the defect and, where at least one of the dimensions and the area of a detected defect is greater than a pre-set acceptable limit, to generate a signal indicating that the object should be rejected.

17. A method as claimed in claim 11 wherein a plurality of the said objects are inspected in parallel by a plurality of inspection systems.

18. A method as claimed in claim 17 wherein the objects are conveyed as a single procession of objects before and after the inspection of objects in parallel.

19. A method as claimed in claim 11 wherein the rotation of the object is provided by one of a continuously rotating belt and roller means on which the object is supported.

20. A method as claimed in claim 19 wherein simultaneous rotation and translation of the object to be inspected is carried out by use of an arrangement comprising a continuous belt which is moved along a track which is inclined relative to the horizontal plane and a plate extending across a surface of the belt, the object being supported by the belt and the plate.

21. A method as claimed in claim 19 wherein simultaneous rotation and translation of the object to be inspected is carried out by use of an arrangement comprising a continuous belt which is moved along a track which is inclined relative to the horizontal plane and a plate extending across a surface of the belt, the object being supported by the belt and the plate.

22. A method as claimed in claim 11 wherein the incident beam and the scattered beam are at an angle to one another, whereby the position of incidence of the scattered beam on the detector means provides a measure of the depth of the surface of the object from which the incident beam spot is scattered, the detector which produces an output which represents the lateral position of the detected spot formed by the scattered beam which itself is a measure of the depth of the object reflecting surface relative to a datum value.

23. A method as claimed in claim 11 wherein the object is a nuclear fuel pellet.

24. A method as claimed in claim 11 wherein the translation of the spot of the incident beam of radiation is provided by the object, when in a position to be inspected by the spot, along an axis substantially parallel to the axis of the object whereby the object moves past.

25. A method as claimed in claim 11 wherein the translation of the spot of the incidence beam of radiation is provided by moving projection means for protecting the incident beam on the object along an axis substantially parallel to the axis of the object whereby the spot moves along the object.

* * * * *